US009259872B2

(12) United States Patent
Hayes et al.

(10) Patent No.: US 9,259,872 B2
(45) Date of Patent: Feb. 16, 2016

(54) MULTIPARTICULATES

(75) Inventors: Geoffrey Gerard Hayes, Saffron Walden (GB); Vincenzo Martinelli, Cambridge (GB); Hassan Mohammad, Ely (GB); Harjit Tamber, Hitchin (GB); Malcolm Walden, Hardwick (GB); Steve Whitelock, Milton (GB)

(73) Assignee: EURO-CELTIQUE S.A., Luxembourg (LU)

( * ) Notice: Subject to any disclaimer, the term of this patent is extended or adjusted under 35 U.S.C. 154(b) by 2184 days.

(21) Appl. No.: 11/661,478

(22) PCT Filed: Aug. 31, 2005

(86) PCT No.: PCT/GB2005/050140
§ 371 (c)(1),
(2), (4) Date: Jun. 20, 2008

(87) PCT Pub. No.: WO2006/024881
PCT Pub. Date: Mar. 9, 2006

(65) Prior Publication Data
US 2008/0260815 A1    Oct. 23, 2008

(30) Foreign Application Priority Data
Aug. 31, 2004  (GB) .................................. 0419296.9

(51) Int. Cl.
*A61K 8/02*    (2006.01)
*B29C 47/60*   (2006.01)
(Continued)

(52) U.S. Cl.
CPC ............... *B29C 47/60* (2013.01); *A61K 9/1617* (2013.01); *A61K 9/1635* (2013.01);
(Continued)

(58) Field of Classification Search
CPC ............................ A61K 8/0241; A61K 9/145
See application file for complete search history.

(56) References Cited

U.S. PATENT DOCUMENTS 3,758,679 A    9/1973  Seidler
4,861,598 A    8/1989  Oshlack
(Continued)

FOREIGN PATENT DOCUMENTS

EP    0 253 104 A1    1/1988
EP    0 553 392 A1    8/1993
(Continued)

OTHER PUBLICATIONS

Hawley, G.G., "Plasticizer," *The Condensed Chemical Dictionary*, p. 691, Van Norstrand Reinhold Company, United States (1977).
(Continued)

*Primary Examiner* — Benjamin Packard
(74) *Attorney, Agent, or Firm* — Sterne, Kessler, Goldstein & Fox P.L.L.C.

(57) ABSTRACT

Extrusion of a mix containing a pharmaceutically active agent can be achieved using a plasticizing excipient in an amount sufficient to act as plasticizer and also act as lubricant, thereby avoiding the need for inclusion of a lubricant. The invention provides multiparticulates with controlled release properties, substantially free of lubricant. The present invention is preferably directed to extruded multiparticulates containing an opioid such as oxycodone, an ammonium methacrylate copolymer such as Eudragit® RSPO, a plasticizing excipient such as preferably stearyl alcohol and a water permeability modifier such as preferably Eudragit® RLPO. The obtained multiparticulates show a release rate profile which is pH-independent.

28 Claims, 3 Drawing Sheets

(51) Int. Cl.
  *A61K 9/16* (2006.01)
  *A61K 31/485* (2006.01)
  *B29C 47/00* (2006.01)
  *A61K 9/14* (2006.01)

(52) U.S. Cl.
  CPC .......... *A61K 31/485* (2013.01); *B29C 47/0011* (2013.01); *B29C 47/6093* (2013.01); *A61K 9/145* (2013.01); *A61K 9/146* (2013.01)

(56) References Cited

U.S. PATENT DOCUMENTS

| | | |
|---|---|---|
| 4,970,075 A | 11/1990 | Oshlack |
| 5,266,331 A | 11/1993 | Oshlack et al. |
| 5,286,493 A | 2/1994 | Oshlack et al. |
| 5,378,462 A | 1/1995 | Boedecker et al. |
| 5,508,042 A | 4/1996 | Oshlack et al. |
| 5,549,912 A | 8/1996 | Oshlack et al. |
| 5,580,578 A | 12/1996 | Oshlack et al. |
| 5,639,476 A | 6/1997 | Oshlack et al. |
| 5,656,295 A | 8/1997 | Oshlack et al. |
| 5,849,240 A | 12/1998 | Miller et al. |
| 5,858,412 A | 1/1999 | Staniforth et al. |
| 5,891,471 A | 4/1999 | Miller et al. |
| 5,958,452 A | 9/1999 | Oshlack et al. |
| 5,965,161 A | 10/1999 | Oshlack et al. |
| 5,965,163 A | 10/1999 | Miller et al. |
| 6,063,313 A | 5/2000 | Briskin et al. |
| 6,103,261 A | 8/2000 | Chasin et al. |
| 6,143,322 A | 11/2000 | Sackler et al. |
| 6,143,353 A | 11/2000 | Oshlack et al. |
| 6,159,501 A | 12/2000 | Skinhoj |
| 6,162,467 A | 12/2000 | Miller et al. |
| 6,261,599 B1 | 7/2001 | Oshlack et al. |
| 6,319,520 B1 | 11/2001 | Wuthrich et al. |
| 6,335,033 B2 | 1/2002 | Oshlack et al. |
| 6,696,088 B2 | 2/2004 | Oshlack et al. |
| 6,706,281 B2 | 3/2004 | Oshlack et al. |
| 6,716,449 B2 | 4/2004 | Oshlack et al. |
| 6,743,442 B2 | 6/2004 | Oshlack et al. |
| 7,070,806 B2 | 7/2006 | Oshlack et al. |
| 7,510,727 B2 | 3/2009 | Oshlack et al. |
| 7,740,881 B1 | 6/2010 | Sackler et al. |
| 2001/0008639 A1 | 7/2001 | Oshlack et al. |
| 2001/0019725 A1 | 9/2001 | Miller et al. |
| 2002/0006438 A1 | 1/2002 | Oshlack et al. |
| 2002/0018810 A1 | 2/2002 | Oshlack et al. |
| 2003/0099704 A1 | 5/2003 | Oshlack et al. |
| 2003/0157168 A1 | 8/2003 | Breder et al. |
| 2003/0190358 A1 | 10/2003 | Oshlack et al. |
| 2004/0028743 A1 | 2/2004 | Wuthrich et al. |
| 2004/0043996 A1 | 3/2004 | Nadkarni |
| 2004/0081694 A1 | 4/2004 | Oshlack et al. |
| 2004/0096500 A1 | 5/2004 | Oshlack et al. |
| 2004/0105887 A1 | 6/2004 | Oshlack et al. |
| 2004/0170680 A1 | 9/2004 | Oshlack et al. |
| 2004/0176402 A1 | 9/2004 | Oshlack et al. |
| 2004/0185098 A1 | 9/2004 | Oshlack et al. |
| 2004/0266807 A1 | 12/2004 | Oshlack et al. |
| 2005/0013862 A1 | 1/2005 | Tobyn et al. |
| 2005/0020613 A1 | 1/2005 | Boehm et al. |
| 2005/0089568 A1 | 4/2005 | Oshlack et al. |
| 2006/0057210 A1 | 3/2006 | Oshlack et al. |
| 2006/0099255 A1 | 5/2006 | Oshlack et al. |
| 2006/0165790 A1 | 7/2006 | Walden et al. |
| 2006/0165791 A1 | 7/2006 | Oshlack et al. |
| 2006/0165792 A1 | 7/2006 | Oshlack et al. |
| 2006/0182801 A1 | 8/2006 | Breder et al. |
| 2009/0148517 A1 | 6/2009 | Oshlack et al. |
| 2010/0172974 A1 | 7/2010 | Oshlack et al. |

FOREIGN PATENT DOCUMENTS

| | | |
|---|---|---|
| EP | 0 631 781 A1 | 1/1995 |
| EP | 0 654 263 A1 | 5/1995 |
| EP | 1 623 703 A1 | 2/2006 |
| JP | 4-112824 | 4/1992 |
| JP | 9-509176 A | 9/1997 |
| JP | 2001-31591 A | 2/2001 |
| WF | 96/14058 | 5/1996 |
| WO | 93/10765 | 6/1993 |
| WO | 93/11749 | 6/1993 |
| WO | WO 97/45091 A2 | 12/1997 |
| WO | 01/32148 A1 | 5/2001 |
| WO | 01/58447 | 8/2001 |
| WO | 01/58451 A1 | 8/2001 |
| WO | 02/087512 | 11/2002 |
| WO | 03/013433 | 2/2003 |
| WO | 2004/093801 | 11/2004 |
| WO | 2005/000310 | 1/2005 |
| WO | 2005/079760 | 9/2005 |

OTHER PUBLICATIONS

The European Pharmacopoeia—$4^{th}$ Edition, "Ammonio Methacrylate Copolymer (Type A)" and "Ammonio Methacrylate Copolymer (Type B)," *Pharmeuropa 14*: pp. 363-365 (Apr. 2002).

"Specifications and test methods for EUDRAGIT® RL 100 and EUDRAGIT® RL PRO, EUDRAGIT® RS 100 and EUDRAGIT® RS PO," *Evonik Industries*, 6 pages, Darmstadt, Germany (2007).

Faulitrillo, C., et al., "Polyvinylpyrrolidone. Povidone. (PVP)," in *Tratado de Farmacia Galenica*, $1^{st}$ Edition, pp. 206 and 207, Spain (1993).

Lee and Robinson, "The Physical Approach: Oral and Parenteral,"in *Sustained and Controlled Release Drug Delivery Systems*, Robinson, J.R., Ed., pp. 138-139, Marcel Dekker, Inc., United States (1978).

Lee, T.W-Y. and Robinson, J.R., "Controlled Release Drug Delivery Systems, " in *Remington: The Science and Practice of Pharmacy*, 20 Edition, Gennaro, A.R., Ed., Chapter 47: 903-905, Lippincott Williams & Wilkins, United States (2000).

"Oxycontin—Controlled Release Oxycodone Hydrochloride," *Ache 10*: 24-26 (2002).

"Pharmaceutics," p. 415, English language translation (1980).

Non-Final Office Action dated Oct. 23, 2008 by the U.S. Patent and Trademark Office in U.S. Appl. No. 11/314,464, filed Dec. 20, 2005, Walden et al.

Final Office Action dated Jul. 31, 2009 by the U.S. Patent and Trademark Office in U.S. Appl. No. 11/314,464, filed Dec. 20, 2005, Walden et al.

Non-Final Office Action dated Jan. 5, 2010 by the U.S. Patent and Trademark Office In U.S. Appl. No. 11/314,464, filed Dec. 20, 2005, Walden et al.

Final Office Action dated Nov. 4, 2010 by the U.S. Patent and Trademark Office in U.S. Appl. No. 11/314,464, filed Dec. 20, 2005, Walden et al.

Non Final Office Action dated Jun. 19, 2013, by the U.S. Patent and Trademark Office in U.S. Appl. No. 11/314,464, filed Dec. 20, 2005, Walden et al.

Final Office Action dated May 7, 2014 by the U.S. Patent and Trademark Office in U.S. Appl. No. 11/314,464, filed Dec. 20, 2005, Walden et al.

Zhang, Y., et al., "A novel pulsed-release system based on swelling and osmotic pumping mechanism," *Journal of Controlled Release 89*:47-55, Elsevier Sciences Publishers, Netherlands (2003).

Aitken-Nichol, C., et al., "Hot Melt Extrusion of Acrylic Films," *Pharmaceutical Research 13*(5):804-808, Plenum Publishing, United States (1996).

Follonier, N., et al., "Evaluation of Hot-Melt Extrusion as a New Technique for the Production of Polymer-Based Pellets for Sustained Release Capsules Containing High Loadings of Freely Soluble Dugs," *Drug Development and Industrial Pharmacy 20*(8):1323-1339, Marcel Dekker, Inc., United States (1994).

(56) References Cited

OTHER PUBLICATIONS

Wu, C. and McGinity, J.W., "Influence of methylparaben as a solid-state plasticizer on the physiochemical properties of Eudragit® RS PO hot-melt extrudates," *European Journal of Pharmaceutics and Biopharmaceutics* 56:95-100, Elsevier Science B.V., Netherlands (2003).

Zheng, W., et al., "Properties of theophylline tablets powder-coated with methacrylate ester copolymers," *J. Drug. Del. Sci. Tech.* 14(4):319-325, Association de pharmacie galenique industrielle, France (Jul. 2004).

Zhu, Y., et al., "Solid-state plasticization of an acrylic polymer with chlorpheniramine maleate and triethyl citrate," *International Journal of Pharmaceutics* 241: 301-310, Elsevier Science, B.V., Netherlands (2002).

English language machine translation of Faulitrillo, C., et al., "Polyvinylpyrrolidone. Providone. (PVP), " in *Tratado de Farmacia Galencia, 1st* Edition, pp. 206 and 207, Spain (1993) (cited here with as NPL4).

Non-Final Office Action dated Feb. 20, 2015 by the U.S. Patent and Trademark Office in U.S. Appl. No. 11/314,464, filed Dec. 20, 2005, Walden et al.

MULTIPARTICULATES

The present invention relates to a process for the production of extruded pharmaceutical products, especially multiparticulates, and in particular to extruded products, especially multiparticulates which provide controlled release of pharmaceutically active ingredients.

BACKGROUND OF THE INVENTION

Extrusion processing to produce controlled release pharmaceutical preparations is perceived as having the advantages of reducing the process steps needed to manufacture the preparations as well as enabling the manufacture to be carried out on a continuous or semi-continuous basis. Such extrusion of a softened blend including an active agent is usually referred to as melt extrusion. The backbone of melt extrusion technology is the application of thermoplastic materials which act as binders for embedded drugs in solution or dispersion form within a matrix. Thermoplastic polymers with low glass transition temperatures (Tg) are preferred for processing by melt extrusion. Lower processing temperatures are preferred with respect to the stability of heat sensitive drugs and other necessary excipients. Polymer glass transition temperatures can be reduced to facilitate processing at lower temperatures by optional addition of plasticisers.

By selection of suitable polymers and additives, melt extrusion technology can be used both to enhance the solubility, and subsequently the bioavailability, of poorly water soluble drugs as well as to retard drug release of moderate to highly water soluble drugs for controlled release products.

Multiparticulates of uniform dimensions with modified drug release properties can readily be manufactured by such melt extrusion technology.

Illustratively WO 96 14058 describes a melt extrusion method of preparing a sustained-release pharmaceutical extrudate suitable for oral administration. The method comprises:

blending a therapeutically active agent together with (1) a material selected from the group consisting of alkylcelluloses, acrylic and methacrylic acid polymers and copolymers, shellac, zein, hydrogenated castor oil, hydrogenated vegetable oil, and mixtures thereof and (2) a fusible carrier selected from the group consisting of natural or synthetic waxes, fatty acids, fatty alcohols, and mixtures thereof; said retardant material having a melting point between 30-200° C. and being included in an amount sufficient to further slow the release of the therapeutically active agent;

heating said blend to a temperature sufficient to soften the mixture sufficiently to extrude the same;

extruding said heated mixture as a strand having a diameter of from 0.1-3 mm; cooling said strand; and dividing said strand to form non-spheroidal multi-particulates of said extrudate having a length from 0.1-5 mm; and dividing said non-spheroidal multi-particulates into unit doses containing an effective amount of said therapeutically active agent, said unit dose providing a sustained-release of said therapeutically active agent for a time period of from about 8 to about 24 hours.

In the worked Examples used to describe this method, stearic acid is employed as a lubricant in the extruded formulation. For instance in Examples 1 to 6 the formulation contains 20% by weight of stearic acid, the controlled release material being variously ethylcellulose and Eudragit RS PO. Extrusion temperatures are in the range of 85° C. to 105° C.

A disadvantage of thermoplastic material, however, is that the Tg may be too high to enable processing to be carried out at temperatures low enough to avoid degradation of the active ingredient and/or excipients.

One solution used to mitigate this problem has been to add excipient material which has a plasticising effect and thus lowers the Tg of the thermoplastic polymer. It serves to reduce cohesion by providing internal lubrication of the polymer.

In our co-pending PCT patent application PCT WO 2005/000310 of 27 Jun. 2004 entitled Multiparticulates, we describe examples of formulations in which relatively high levels of a plasticiser, especially stearyl alcohol, and a lubricant, namely stearic acid, are used together with acrylic copolymers and oxycodone hydrochloride as active ingredient. The temperatures required to extrude these formulations are typically in the range 75° C. to 95° C. At such temperatures it was found that the extrudate had good chemical stability after storage under accelerated storage conditions (40° C./75% RH) but the release rate of the active agent from the formulation was found in in vitro testing to change over time. Initially, stearic acid was found to have an influence on release rates in buffers of different pHs, and therefore a search was made for alternative lubricants. Glyceryl behenate was found to be effective.

A need remains for the availability of new processes and formulations which will allow the extrusion of controlled release formulations at relatively low to moderate temperatures which do not give rise to the risk of degradation of heat sensitive or heat labile active ingredients or other components of the formulation, for example in the range 75° C. to 95° C., as well as allowing the extrusion of formulations from which conventional components which may result in release rate instability can be excluded.

SUMMARY OF THE INVENTION

We have surprisingly found that excipients exhibiting a plasticising effect may also have useful lubricating properties. The lubrication reduces the adhesion of the matrix material in an extruder to the extrusion chamber walls, the orifice walls, and the surfaces of the screws and other elements in the extruder. The effect of this reduction allows for the torque required for extrusion and the power which has to be supplied to the motor to be reduced.

More particularly, in connection with the investigations resulting in WO 2005/000310, we found unexpectedly that by totally eliminating the lubricant component and increasing the plasticiser concentration, extruded formulations were obtained which had increased pH dissolution stability. However some thermal dissolution instability was found. Reducing the concentration of plasticiser reduced the thermal dissolution instability but led to the requirement for higher processing temperatures and increased torque. Surprisingly we found that by suitable adjustment of the plasticiser concentration, processing could be carried out at low to moderate temperatures to produce extruded products having good thermal dissolution stability and good pH dissolution stability.

According to the present invention, we provide a plurality of particles, referred to as multiparticulates, containing a pharmaceutically active agent. The pharmaceutically active agent is usually in the form of a pharmaceutically acceptable salt. The multiparticulates can be made by extrusion without the need to include a lubricant additional to a plasticiser.

In one aspect, the present invention provides a method of preparing an extruded pharmaceutical composition which comprises selecting a plasticising excipient that provides plasticising and lubricating properties, and extruding a mix including a pharmaceutically active agent and the plasticising excipient, said plasticising excipient being employed in an amount effective to act as a plasticiser for the mix and to act as a lubricant for the mix. Preferably the mix is substantially free of further excipient acting to lubricate the mix.

Thus, by the invention, it is possible to prepare multiparticulates containing a pharmaceutically active agent and a plasticising excipient with lubricating properties, substantially free of further lubricant.

The multiparticulates of this invention employ a plasticiser to act secondarily as a lubricant. Thus, for example, the multiparticulates contain a pharmaceutically active agent, an ammonium methacrylate copolymer, a plasticiser which is a non-dominating plasticiser, and a water permeability modifier. By non-dominating plasticiser we mean a plasticiser which when added in an amount so as predominantly to affect the glass transition temperatures (Tg) and the thermoplastic melt viscosity in order to enable extrusion at low to moderate temperatures through a die-head orifice, also has sufficient lubricating properties to avoid producing unnecessary stress on the extruder which may be caused by increased torque and power supply to the motor.

In a specific aspect, multiparticulates of the invention contain or consist essentially of the pharmaceutically active agent, which is preferably oxycodone and which is usually in the form of a pharmaceutically acceptable salt, an ammonium methacrylate copolymer, a water permeability modifier and a non-dominating plasticiser.

The water permeability modifier is preferably a pH-independent water permeability modifier. More particularly, we prefer that the solubility of the water permeability modifier is substantially the same in gastric and intestinal environments.

The multiparticulates of this invention do not contain a dominating or non-dominating lubricant, in an amount which at least provides a significant amount of the lubrication during processing. By dominating lubricant we mean a material which significantly reduces adhesion of the thermoplastic polymer to the extruder surfaces without significantly reducing the Tg of the thermoplastic polymer. A non-dominating lubricant will predominantly reduce the adhesion but will also reduce Tg to some degree.

The multiparticulates of this invention can be used as a fill in a capsule. Thus, the present invention provides a capsule suited for once or twice a day dosing. Other dosage forms of the controlled release formulation can be provided.

In a further aspect of the invention, there is provided a method of treating a patient with a controlled release formulation of this invention. The method includes administering a dosage form of this invention, preferably one containing oxycodone or a salt thereof, to a patient in need of appropriate therapy, especially oxycodone analgesic therapy. In a related aspect, the invention provides a method of providing analgesia to a patient which comprises administering an effective amount of a controlled release formulation comprising multiparticulates of the invention wherein the pharmaceutically active agent is an analgesic. The invention further extends to the use of an analgesic pharmaceutically active agent in the preparation of a unit dose for a method of providing analgesia to a patient, which method comprises administering an effective amount of a controlled release formulation comprising multiparticulates of the invention wherein the pharmaceutically active agent is an analgesic The multiparticulates are preferably obtainable by extrusion of an extrudable blend. Such an extrusion can be of the kind disclosed in WO 9614058 and referred to as a melt extrusion. In practice, the polymer softens but in practice might not melt.

In a related aspect, we provide a process for preparing multiparticulates containing an active agent, preferably oxycodone or a salt thereof, which comprises extrusion of an extrudable blend of active agent usually in the form of a pharmaceutically acceptable salt, an ammonium methacrylate copolymer, a non-dominating plasticiser, and a water permeability modifier.

A preferred process of this invention comprises extruding an extrudable blend to form the multiparticulates, using one or more plasticisers which also act as the lubricant.

The invention further resides in a method of avoiding heat degradation in an extrusion of an extrudable blend comprising a heat-sensitive pharmaceutically active agent, an ammonium methacrylate copolymer, a plasticiser, a lubricant and a water permeability modifier, which method comprises selecting a sufficient amount of plasticiser which also acts as the lubricant. In a related aspect, the present invention provides a method of extruding an extrudable blend comprising a pharmaceutically active agent sensitive to heat, which involves using a sufficient amount of a plasticiser which acts also as the lubricant and avoids the need for extrusion at high temperatures by sufficiently reducing cohesive and adhesive forces.

DETAILS OF THE INVENTION

The preferred multiparticulates of this invention contain (a) active agent, (b) water-insoluble ammonium methacrylate copolymer, (c) non-dominating plasticiser, and (d) water permeability modifier.

Active agents which may be used in the formulations and processes of the invention are preferably those which are heat sensitive at temperatures above say 95-100° C. Such active agents include for example opioids, HMGCoA reductase inhibitors (statins) and antibiotics.

Candidate opioids or opiates include alfentanil, allylprodine, alphaprodine, anileridine, benzylmorphine, bezitramide, buprenorphine, butorphanol, clonitazene, codeine, cyclazocine, desomorphine, dextromoramide, dezocine, diacetylmorphine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, levophenacylmorphan, lofentanil, meperidine, meptazinol, metazocine, methadone, metopon, morphine, morphine-6-glucuronide, myrophine, nalbuphine, narceine, nicomorphine, norlevorphanol, normethadone, normorphine, norpipanone, noroxymorphone, opium, oxycodone, oxymorphone, papavereturn, pentazocine, phenadoxone, phenomorphan, phenazocine, phenoperidine, piminodine, piritramide, propheptazine, promedol, properidine, propiram, propoxyphene, remifentanil, sufentanil, tilidine, tramadol, and pharmaceutically acceptable salts.

Preferred opioids/opiates are: buprenorphine, codeine, dihydrocodeine, dihydromorphine, fentanyl, hydrocodone, hydromorphone, morphine, oxycodone, oxymorphone and tramadol, and pharmaceutically acceptable salts.

Candidate hydroxymethylglutaryl coenzyme A reductase inhibitors include atorvastatin, 6-[4,4-bis(fluorophenyl)-3-(1-methyl-1H-tetrazol-5-yl)-1,3-butadienyl]-3,4,5,6-tetrahydro-4-hydroxy-2H-pyran-2-one, 3-(12-carboxy-12-methyltridecyl)-3-hydroxyglutaric acid, cerivastatin, dalvastatin, 3,5-dihydroxy-9,9-diphenyl-6,8-nonadienoic acid methyl ester, fluindostatin, fluvastatin, 6-[2-(4'-fluoro-3, 3',5-trimethyl-2-biphenylyl)vinyl]-4-hydroxy-2-oxotetrahydropyran, 6-[2-[4-(4-fluorophenyl)-2-isopropyl-6-phenyl-3-pyridyl]vinyl]-3,4,5,6-tetrahydro-4-hydroxy-2H-pyran-2-one, lovastatin, mevastatin, mevinolinic acid, monacolin J, monacolin L, pitavastatin, pravastatin, rosuvastatin, simvastatin, and pharmaceutically acceptable salts.

Candidate antibiotics include aminoglycosides, e.g. amikacin, gentamicin, neomycin, netilmicin, tobramycin; carbapenems, e.g. imipenem, meropenem; cephalosporins, e.g. cefaclor, cefadroxil, cefamandole, cefixime, cefotaxime, cefpirome, cefpodoxime, cefprozil, ceftazidime, ceftriaxone, cefuroxime, cephalexin, cephazolin, cephradine; cephamycins, e.g. cefoxitin; folic acid inhibitors, e.g. trimethoprim; lincosamides, e.g. clindamycin; macrolides, e.g. azithromycin, clarithromycin, erythromycin, telithromycin; monobactams, e.g. aztreonam; nitroimidazoles, e.g. metronidazole, timidazole; penicillins, e.g. amoxycillin, ampicillin, piperacillin, penicillin G, flucloxacillin, ticarcillin; quinolones, e.g. ciprofloxacin, levofloxacin, nalidixic acid, ofloxacin; streptogramin, e.g. quinupristin/dalfopristin; sulphonamides, e.g. sulfametopyrazine; and tetracyclines, e.g. demeclocycline, doxycycline, lymecycline, minocycline, oxytetracycline, tetracycline, chlortetracycline, and pharmaceutically acceptable salts.

The preferred active agent is oxycodone, either the free base or its pharmaceutically acceptable salts, especially the hydrochloride. For further information on oxycodone we refer to our co-pending PCT patent application WO 2005/000310 entitled Multiparticulates, which is incorporated herein by reference. Another preferred active agent is oxymorphone, either the free base or a pharmaceutically acceptable salt thereof; especially the hydrochloride salt.

The water-insoluble ammonium methacrylate copolymer, also referred to as a water-insoluble ammonio methacrylate copolymer, is suitably Eudragit RS PO or Eudragit RS 100 milled to a fine powder. It offers the following properties:
insoluble to poorly water soluble,
low aqueous permeability,
has demonstrated compatiblility with a variety of drugs and other additives,
extrudable at moderate temperatures without decomposition or at lower temperatures in the presence of a suitable plasticiser,
stable for the intended storage time and conditions,
thermal stability.

In particular, Eudragit RS PO is a thermoplastic copolymer of low water permeability which can significantly retard release of embedded oxycodone in its matrix. It is described as a pH independent polymer powder with low permeability for matrix formulations. It is a copolymer of acrylic and methacyrylic acid esters, with a low content of quaternary ammonium groups to control permeability, and an average molecular weight of around 150,000.

The non-dominating plasticiser serves to soften the insoluble ammonium methacrylate copolymer to make it more easy to extrude the copolymer. To this end, the typical plasticiser is miscible with the insoluble ammonium methacrylate copolymer to produce a decreased tensile strength, a lower softening temperature, and a decrease in the glass transition temperature, $T_g$, of the polymer. It serves to reduce cohesion by providing internal lubrication of the polymer. The plasticiser is normally chosen from water insoluble solids such as cetyl alcohol, stearyl alcohol and cetostearyl alcohol; water soluble solids such as sorbitol and sucrose and high molecular weight polyethylene glycol; water insoluble liquids such as dibutyl sebacate and tributyl citrate and water soluble liquids such as triethyl citrate, propylene glycol and low molecular weight polyethylene glycol. Plasticisers which are solid at room temperature are preferred. Stearyl alcohol is a preferred plasticiser. Another preferred plasticiser is a high molecular weight polyethylene glycol, preferably with a molecular weight in the range 4000 to 10000, such as PEG 6000.

More generally, other plasticisers which may be used according to the invention include plasticisers which can mimic one of the indicated typical plasticisers. Such other plasticisers thus have plasticising and lubricating properties approximating to those of a material chosen from cetyl alcohol, stearyl alcohol, cetostearyl alcohol, sorbitol, sucrose, high molecular weight polyethylene glycol preferably with a molecular weight in the range 4000 to 10000, e.g. PEG 6000, dibutyl sebacate, tributyl citrate, triethyl citrate, propylene glycol and low molecular weight polyethylene glycol. For example, suitable other plasticisers have plasticising and lubricating properties approximating to those of cetyl alcohol, or of stearyl alcohol, or of cetostearyl alcohol, or of sorbitol, or of sucrose, or of high molecular weight polyethylene glycol preferably with a molecular weight in the range 4000 to 10000, e.g. PEG 6000, or of dibutyl sebacate, or of tributyl citrate, or of triethyl citrate, or of propylene glycol, or of low molecular weight polyethylene glycol. Approximation to stearyl alcohol or PEG 6000 is preferred.

Plasticisers with plasticising and lubricating properties that approximate to such a typical plasticiser can be identified by the following criteria:
(a) when tested for plasticising effect by Differential Scanning Calorimetry at a given concentration in Eudragit RS PO, will reduce the $T_g$ (measured as ° C.) of the Eudragit polymer by within ±50% of the reduction provided by the same concentration of the typical plasticiser;
(b) when tested for lubricating effect in an IKA® MKD 0,6-H 60 High-performance measuring kneader at a given concentration in Eudragit RS PO, will reduce the torque (measured as Nm) by within ±50% of the reduction provided by the same concentration of the typical plasticiser; where the values of Tg and torque are the mean of three test results.

Preferably the reduction in (a) is within ±25% of the reduction provided by the typical plasticiser.

Preferably the reduction in (b) is within ±25% of the reduction provided by the typical plasticiser.

Thus, suitable other plasticisers can be employed which give the plasticising effect of test (a), and the lubricating effect of test (b).

The water permeability modifier modulates secretion of the drug from the dosage form. Typically the water permeability modifier serves to enhance the drug release, especially in the later stages of the dissolution, though we also envisage that the water permeability modifier might in some instances play a role in slowing release. Examples of agents used to modify the water permeability of the extruded multiparticulates include an insoluble hydrophilic wicking agent, a gelling agent which hydrates to form a gel to control the water movement, a high molecular weight polyethylene glycol such as PEG 6000, or a water permeable ammonium methacrylate copolymer, also referred to as an ammonio methacrylate copolymer, such as Eudragit RL PO or Eudragit RL 100 milled to a fine powder. Eudragit RL PO is described as a highly permeable pH independent polymer powder for matrix formulations. It is a copolymer of acrylic and methacyrylic acid esters, with a content of quaternary ammonium groups to provide permeability, and an average molecular weight of around 150,000.

For example, microcrystalline cellulose, high molecular weight hydrogels such as high viscosity hydroxypropylmethyl cellulose and high viscosity poly(ethylene oxide), and water permeable ammonium methacrylate copolymers may be used to enhance the total release of the active. In this last respect, the ammonium methacrylate copolymer employed as agent (d) to modify the water permeability is not the same copolymer as the water insoluble ammonium methacrylate copolymer used as ingredient (b), being more water permeable due to different degrees of substitution by quaternary ammonium groups.

Microcrystalline cellulose improves water diffusion and exchange and thus enhances drug release. The microcrystalline cellulose acts as an insoluble but hydrophilic wicking agent. Alternatives to microcrystalline cellulose are croscarmellose sodium, crospovidone or sodium starch glycollate.

High molecular weight grade (high viscosity) hydroxypropylmethyl cellulose (HPMC) initially hydrates to form a thick gel to control the water movement. The hydrated gel then gradually dissolves and/or erodes over time leaving a porous and highly permeable structure. According to this hypothesis, it is believed that high viscosity HPMC does not significantly increase drug release at the earlier hours but enhances the release at later time points. Other gelling agents are candidates, including polyethylene oxide, pectin, locust bean gum or xanthan gum.

Eudragit RL PO is a highly water permeable analogue and can significantly enhance the release rate and total drug release.

Suitable percentage amounts for the ingredients (a) to (d) are given in the following table, based on the total weight of the four ingredients:

| | typical range | preferred range | most preferred range |
| --- | --- | --- | --- |
| active agent | 3 to 50 | 5 to 40 | 8 to 30 |
| insoluble ammonium methacrylate copolymer | 25 to 85 | 35 to 75 | 55 to 70 |
| non-dominating plasticiser | 1 to 30 | 3 to 25 | 10 to 20 |
| water permeability modifier | 1 to 30 | 3 to 25 | 10 to 20 |

Other additives may also be employed to produce multiparticulates within a set of predetermined specifications. Bulking agents, for example lactose and calcium phosphate, are widely used pharmaceutical excipients and can be used in the present invention to modify the release rates and/or total release. Other release modifying agents may also be considered to modulate the release rate and/or enhance total release. Antioxidants, such as butylated hydroxytoluene, may also be used to stabilise formulations of the present invention by preventing or reducing chemical degradation of heat sensitive or heat labile active ingredients or excipients at higher manufacturing temperatures The multiparticulates of the present invention do not include an amount of a dominating or non-dominating lubricant sufficient to provide a significant or useful amount of the lubrication during processing. Typical dominating and non-dominating lubricants are solids, such as stearic acid, glyceryl behenate, magnesium stearate, calcium stearate, talc or silicone dioxide (fused silica).

A particularly preferred formulation comprises 7.5 to 9% w/w, preferably about 8.3% w/w, oxycodone hydrochloride; 55 to 70% w/w, preferably about 61.7% w/w, Eudragit RS PO; 10 to 20% w/w, preferably about 15% w/w, Eugragit RL PO; and 10 to 20% w/w, preferably about 15% w/w, stearyl alcohol.

Furthermore, requirements for providing a twice-a-day capsule in 40 mg and 80 mg strengths using size 1 capsules led to further re-assessment of the drug load and in this connection we have identified the following suitable percentage amounts for the ingredients (a) to (d) given in the following table, based on the total weight of the four ingredients:

| | typical range | Preferred range | most preferred range |
| --- | --- | --- | --- |
| active agent, preferably oxycodone hydrochloride | 25 to 32 | 29 to 31 | about 30, for example 30.3 |
| insoluble ammonium methacrylate copolymer | 25 to 85 | 35 to 75 | 50 to 60 |
| non-dominating plasticiser | 1 to 30, e.g. 1 to 10 | 3 to 25 | 5 to 15 |
| water permeability modifier | 1 to 30, e.g. 10 to 20 | 3 to 25 | 3 to 15 |

Preferred formulations, e.g. containing 8.3% w/w oxycodone hydrochloride, according to this invention, when stored for up to 3 months at 25° C./60% relative humidity, "RH", or 30° C./65% RH, show no or negligible change in dissolution when tested according to the methods disclosed herein. When tested at 40° C./75% RH a minor change in dissolution, e.g. with a reduction by 3 to 5%, has been observed after one month's storage which, however, has not further changed upon continued storage.

In the process of the invention the ingredients are blended, and extruded. Details of such procedures are given in WO 9614058, which is incorporated herein in full by specific reference.

For the present invention, we prefer to employ a twin screw extruder, which can have co-rotating or counter-rotating screws. Essentially, the blend as a powder is fed by a feeder into the first segment of the barrel usually at relatively low temperature, for example 10-20° C., to ensure a constant powder flow to the high temperature barrels. The feeder provides a uniform current of the blend to the extruder. Consistency is desirable as irregular and variable feeding rates can produce multiparticulates with varying physical properties, such as density and porosity.

The preferred extruder is designed with twin screws, preferably counter-rotating screws, for the task of conveying, blending, compressing, heating and softening the blend. Depending on the choice of the components of the blend and the extrusion conditions, it may be that the blend will melt as well as soften. The screws which perform a significant part of this extrusion process are built of different smaller elements chosen from a variety of screw elements and kneader elements. Mixing and kneading time can be significantly altered by changing the type, length and configuration of the screw elements and possibly kneader elements. Short residence times and moderate to low shear forces contribute to safe processing and stable product even with heat sensitive drugs. Examples of available extruders include those manufactured by Leistritz, Brabender, Randcastle, and Kurimoto Co. Ltd, for example a Leistritz Micro 18 machine.

Screw rotating speeds may play a part in the quality of the multiparticulates produced. High rotation speeds without appropriate compensation of the blend feed rate may produce high porosity multiparticulates with a variable drug release rate. On the other hand slow screw rotation would induce unnecessary long residence times. A vacuum connected to the extruder barrel is desirable to remove trapped air within the softened blend and thus produce dense low porosity multiparticulates.

The extrusion head is typically designed to produce multiple strands of fixed diameter. The number, shape and diameter of the orifices can be changed to suit a predetermined specification.

In addition to the screw speed, the other main influential parameters are the screw torque, individual barrel temperature, and extrusion head pressure and temperature.

In accordance with one cutting procedure of this invention, the extruded strands are carried away from the die-head on a conveyer. The strand diameter is affected by the blend feed rate, screw speed, barrel temperature, die-head design and orifice diameter, conveying speed and nip rolls speed. Conveying is appropriate to carry the extruded strand to a laser gauge or other measuring device to monitor a desired diameter such as 1.0 mm. During this conveying process the strands cool down gradually, but essentially remain flexible. Flexible strands retain integrity on the laser gauging device, between the pelletiser feed nip rolls and during entry to the pelletiser. Rapidly cooled strands, depending on the formulation, may lose their integrity and shatter during passage through the nip rolls and pelletiser into uneven-shaped and irregular-sized multiparticulates.

The strands are fed into the pelletiser by nip rolls. The pelletiser cuts the fed strands, for instance using a rotary knife cutter, to a pre-determined length, for example 1.0 mm. The feeding rate of the strands and the pelletiser cutter speed determine the length of the multiparticulates.

Overall, the co-ordination/interaction between the powder feeder, extruder, conveyor, laser gauge and pelletiser is an important parameter affecting the quantity, quality and reproducibility of the final multiparticulate products.

Multiparticulates produced by this cutting procedure where the extruded strands are carried away from the die-head typically take the form of cylinders.

In another preferred cutting procedure, a cutter cuts the extruded mix as it emerges under pressure and still softened from the orifices of the die plate. The cutter is suitably a rotary cutter with one or more blades which sweep over the surface of the die-head to pass the orifices. Two diametrically opposed blades are preferred. Ideally, the inner and outer surface boundaries to the extrusion orifices are coated with a non-stick material, e.g. a polytetrafluoroethylene (PTFE). As the cut extrudate particles expand and cool, they tend to form rounded surfaces. By appropriate adjustment of the die-head extrusion pressure, the rate of extrusion, the die-head design and orifice diameter and number of orifices, and the speed of the cutter blade, it is possible to arrange for spherical or near-spherical multiparticulates to be obtained. Alternatively, this process can be operated to produce rods if desired. In one embodiment a stream of air is directed at the surface of the die-head, the air being at a reduced temperature to cool the extrudate and speed solidification, thereby reducing stickiness.

Spherical multiparticulates produced by this method offer a number of possible advantages:
Better batch to batch reproducibility.
Easier coating and lower coating weight required.
Better capsule filling and higher yield.
More stable at elevated storage temperature.
More tamper resistant.
Reduced downstream processing.
Reduce or eliminate some problems that arise during conveying and pelletising the strands such as strands shattering to different length pellets and static charge.

The multiparticulates may be divided into unit doses such that each individual unit dose includes a dose of oxycodone sufficient to provide analgesia to a mammal, preferably a human patient. A suitable dose of oxycodone is 5 to 400 mg, especially 5 mg, 10 mg, 20 mg, 40 mg, 80 mg, 120 mg or 160 mg unit doses. In this respect, a unit dose contains an effective amount of the therapeutically active agent to produce pain relief and/or analgesia to the patient. The dose of oxycodone administered to a patient will vary due to numerous factors, including the weight of the patient, the severity of the pain, the metabolic status and the tolerance, along with the nature of any other therapeutic agents being administered.

In one preferred embodiment, the multiparticulates are filled into hard gelatin capsules each containing a unit dose. The fill weight in the capsule is preferably in the range 80 to 500 mg, more preferably 120 to 500 mg. In a variation of this invention, the unit doses of multiparticulates may be incorporated into other solid pharmaceutical dosage forms, for example using compression or shaping into tablets, by filling into sachets or by forming the extruded product into the form of a suppository.

With the selection of ingredients according to the present invention it becomes possible in a preferred aspect of the invention and as described in embodiments below to prepare multiparticulates and thus capsules containing oxycodone hydrochloride and which mimic the in vitro and preferably the in vivo release characteristics of OxyContin® Tablets. In particular, the combination enables an adequate initial release of oxycodone (early hours) whilst maintaining a high total release of the active ingredient in the later hours of dissolution. Such formulations in a preferred form demonstrate good thermal chemical stability and thermal physical/dissolution rate stability in in vitro testing after storage under accelerated conditions.

Oxycodone hydrochloride is the preferred form of oxycodone, though other pharmaceutically acceptable salts can be used.

Oxycodone is indicated for the treatment of moderate to severe pain. Controlled release oxycodone products enable management of pain when a continuous and around-the-clock supply of analgesic is needed for an extended period of time.

Formulations of oxycodone which provide controlled release of oxycodone are described for instance in WO 9310765. A granulation procedure is typically employed. In Example 3, a tablet containing 10 mg of oxycodone hydrochloride is prepared from a mix of oxycodone hydrochloride, lactose, povidone, Eudragit RS 30 D, triacetin, stearyl alcohol, talc and magnesium stearate. The same ingredients in adjusted amounts are employed in Example 4 to prepare tablets containing 20 mg oxycodone hydrochloride. The resultant products exhibit differing pharmacokinetic and pharmacodynamic properties.

Illustratively, the in vitro release rates of the 10 mg and 20 mg oxycodone tablets are given in WO 9310765 as follows:

| hour | % oxycodone hydrochloride released | |
|---|---|---|
| | 10 mg | 20 mg |
| 1 | 38.0 | 31 |
| 2 | 47.5 | 44 |
| 4 | 62.0 | 57 |

-continued

| | % oxycodone hydrochloride released | |
|---|---|---|
| hour | 10 mg | 20 mg |
| 8 | 79.8 | 71 |
| 12 | 91.1 | 79 |
| 18 | 94.9 | 86 |
| 24 | 98.7 | 89 |

Tablets of this kind and with such release rates form the basis for a commercial product. Controlled release oxycodone tablets are available as OxyContin® Tablets, which are designed to provide controlled delivery of oxycodone over 12 hours.

Oxycodone is well absorbed from OxyContin® Tablets with an oral bioavailability of 60% to 87%. The relative oral bioavailability of OxyContin® Tablets to immediate-release oral dosage forms is 100%. Upon repeated dosing in normal volunteers in pharmacokinetic studies, steady-state levels were achieved within 24-36 hours.

Dose proportionality has been established for 10 mg, 20 mg, 40 mg, 80 mg, and 160 mg tablet strengths with respect to both peak plasma levels ($C_{max}$) and extent of absorption (bioavailability), AUC, as indicated by the following data:

| | | Mean [% coefficient variation] | | | |
|---|---|---|---|---|---|
| Regimen | Dosage Form | AUC (ng · hr/mL)* | Cmax (ng/mL) | Tmax hrs) | Trough Conc. (ng/mL) |
| Single Dose | 10 mg OxyContin ® Tablets | 100.7 [26.6] | 10.6 [20.1] | 2.7 [44.1] | n.a. |
| | 20 mg OxyContin ® Tablets | 207.5 [35.9] | 21.4 [36.6] | 3.2 [57.9] | n.a. |
| | 40 mg OxyContin ® Tablets | 423.1 [33.3] | 39.3 [34.0] | 3.1 [77.4] | n.a. |
| | 80 mg OxyContin ® Tablets** | 1085.5 [32.3] | 98.5 [32.1] | 2.1 [52.3] | n.a. |
| Multiple Dose | 10 mg OxyContin ® Tablets q12h | 103.6 [38.6] | 15.1 [31.0] | 3.2 [69.5] | 7.2 [48.1] |
| | 5 mg immediate-release q6h | 99.0 [36.2] | 15.5 [28.8] | 1.6 [49.7] | 7.4 [50.9] |

*for single-dose AUC = $AUC_{0-inf}$; for multiple dose AUC = $AUC_{0-T}$
**data obtained while volunteers received naltrexone which can enhance absorption Oxycodone is extensively metabolized and eliminated primarily in the urine as both conjugated and unconjugated metabolites. The apparent elimination half-life of oxycodone following the administration of OxyContin® Tablets was 4.5 hours compared to 3.2 hours for immediate-release oxycodone.

About 60% to 87% of an oral dose of oxycodone reaches the central compartment in comparison to a parenteral dose. This high oral bioavailability is due to low pre-systemic and/or first-pass metabolism. In normal volunteers, the $t_{1/2}$ of absorption is 0.4 hours for immediate-release oral oxycodone. In contrast, OxyContin® Tablets exhibit a biphasic absorption pattern with two apparent absorption half-lives of 0.6 and 6.9 hours, which describes the initial release of oxycodone from the tablet followed by a prolonged release.

According to a preferred aspect of the present invention, we provide a plurality of particles of oxycodone, referred to as oxycodone multiparticulates.

In one aspect, we provide oxycodone multiparticulates with a high initial release of oxycodone, and a high total release of oxycodone. The release properties can be expressed in terms of release of oxycodone under controlled in intro conditions which for example simulate human gastric fluids or the human intestinal environment. Release at a physiological pH, for example a pH of about 1.2 or about 6.8, can be tested. Test procedures can also be designed to reflect a switch from the stomach to the intestine during passage through the body.

In particular, we have found that the inclusion of a water permeability modifier can permit extrusion of multiparticulates of oxycodone which show some bioequivalence to OxyContin® Tablets. The multiparticulates can have pharmacokinetic and/or pharmacodynamic properties approximating to those of OxyContin® Tablets. In particular, the multiparticulates can have in vitro release rates that approximate to those of OxyContin® Tablets.

In a related aspect, we provide oxycodone multiparticulates comprising oxycodone usually in the form of a pharmaceutically acceptable salt, an ammonium methacrylate copolymer, a plasticiser which also acts as a lubricant, and a water permeability modifier.

The dosage form using the oxycodone multiparticulates is preferably a unit dosage form, and preferably shows some bioequivalence to OxyContin® Tablets. The dosage form can have pharmacokinetic and/or pharmacodynamic properties approximating to those of OxyContin® Tablets. In particular, the dosage form can have in vitro release rates that approximate to those of OxyContin® Tablets.

The oxycodone multiparticulates of this invention preferably give in vitro release rates that approximate to those of OxyContin® Tablets. The release rates of OxyContin® Tablets are notable for a high initial release, and a high total release. Preferably the release of oxycodone is substantially independent of pH in the pH range of around 1 to around 7. To this end, substantially pH-independent release can mean that for a given formulation when tested in simulated intestinal fluid at pH 6.8, at any given time point the amount of oxycodone released as a percentage of the original amount of oxycodone in the formulation is substantially equal to the percentage amount of oxycodone released based on the original amount of oxycodone in the formulation when tested in simulated gastric fluid at pH 1.2. The release is substantially equal when the respective amounts differ by ±30%, more preferably ±20% and most preferably ±15%.

Unless otherwise indicated, we measure release rates by a specified method which involves using Ph.Eur. basket dissolution apparatus at 37° C., 100 rpm in 900 ml of USP simulated gastric fluid at pH 1.2 without enzyme. In one variation, the dissolution medium is simulated intestinal fluid at pH 6.8 without enzyme.

For simulated gastric fluid at pH 1.2, the oxycodone multiparticulates of this invention typically release at least 15% oxycodone after 1 hour, reflecting a high initial release. Preferably they release at least 20%, more preferably at least 25% and most preferably at least 35% of the oxycodone after 1 hour.

The oxycodone multiparticulates of this invention typically release at least 30% oxycodone after 2 hours, reflecting a high initial release. Preferably they release at least 40%, more preferably at least 50% and most preferably at least 55% of the oxycodone after 2 hours.

The oxycodone multiparticulates of this invention typically release at least 60% oxycodone after 4 hours, reflecting a high initial release. Preferably they release at least 70%, more preferably at least 75% and most preferably at least 80% of the oxycodone after 4 hours.

The oxycodone multiparticulates of this invention typically release at least 75% oxycodone after 10 hours, reflecting a high total release. Preferably they release at least 80%, more preferably at least 90% and most preferably at least 95% of the oxycodone after 10 hours.

Furthermore, at least 85% release of oxycodone after 8 hours is preferred. The oxycodone multiparticulates of this invention can release 100% oxycodone after 12 hours, reflecting a high total release.

The preferred multiparticulates of this invention contain (a) oxycodone, (b) water-insoluble ammonium methacrylate copolymer, (c) plasticiser and (d) water permeability modifier. With this selection of ingredients it becomes possible to prepare multiparticulates and thus capsules containing oxycodone and which mimic the in vitro and preferably the in vivo release characteristics of OxyContin® Tablets. In particular, the combination including a water permeability modifier enables an adequate initial release of oxycodone (early hours) whilst maintaining a high total release of the active ingredient in the later hours of dissolution.

The capsules or other unit dose forms of this invention preferably are designed for administration at intervals of about 12 hours. To this end, the unit dose form suitably has an oxycodone dissolution rate in vitro, when measured by the USP Paddle Method (see the U.S. Pharmacopoeia XXII 1990) at 100 rpm in 900 ml aqueous buffer (pH between 1.6 and 7.2) at 37° C. of between 12.5 and 42.5% (by wt) oxycodone released after 1 hour, between 25 and 56% (by wt) oxycodone released after 2 hours, between 45 and 75% (by wt) oxycodone released after 4 hours and between 55 and 85% (by wt) oxycodone released after 6 hours. Furthermore, we prefer that the peak plasma level of oxycodone obtained in vivo occurs between 2 and 4.5 hours after administration of the dosage form.

More information on desirable characteristics for such oxycodone formulations is given in WO 9310765 which is incorporated herein in full by specific reference.

Using our specified method at pH 1.2, simulated gastric fluid, the release rates are suitably as follows:
Preferred Limits

| Hour | % Released Lower Limit | % Released Upper Limit |
|---|---|---|
| 1 | 16 | 56 |
| 2 | 37 | 77 |
| 4 | 60 | 100 |
| 10 | 75 | 100 |

More Preferable Limits

| Hour | % Released Lower Limit | % Released Upper Limit |
|---|---|---|
| 1 | 21 | 51 |
| 2 | 42 | 72 |
| 4 | 65 | 95 |
| 10 | 80 | 100 |

Most Preferred Limits

| Hour | % Released Lower Limit | % Released Upper Limit |
|---|---|---|
| 1 | 24 | 48 |
| 2 | 45 | 69 |
| 4 | 68 | 92 |
| 10 | 83 | 100 |

Using our specified method at pH 6.8, simulated intestinal fluid, the release rates are suitably as follows:
Preferred Limits

| Hour | % Released Lower Limit | % Released Upper Limit |
|---|---|---|
| 1 | 11 | 51 |
| 2 | 28 | 68 |
| 4 | 48 | 88 |
| 10 | 61 | 100 |

More Preferable Limits

| Hour | % Released Lower Limit | % Released Upper Limit |
|---|---|---|
| 1 | 16 | 46 |
| 2 | 33 | 63 |
| 4 | 53 | 83 |
| 10 | 66 | 96 |

Most Preferred Limits

| Hour | % Released Lower Limit | % Released Upper Limit |
|---|---|---|
| 1 | 19 | 43 |
| 2 | 36 | 60 |
| 4 | 56 | 80 |
| 10 | 69 | 93 |

As an alternative to administration at intervals of about 12 hours, the capsules or other unit dose forms of this invention are designed for administration at intervals of about 24 hours. To this end, the unit dose form suitably has an oxycodone dissolution rate it vitro, when measured by the USP Basket Method at 100 rpm in 900 ml aqueous buffer at a pH between 1.6 and 7.2 at 37° C. of from 0% to about 40% at 1 hour, from about 8% to about 70% at 4 hours, from about 20% to about 80% at 8 hours, from about 30% to about 95% at 12 hours, from about 35% to about 95% at 18 hours, and greater than about 50% at 24 hours. Furthermore, we prefer that the peak plasma level of oxycodone obtained in vivo is reached at about 2 hours to about 17 hours after administration at steady state of the dosage form.

More information on desirable characteristics for such oxycodone formulations is given in WO 02087512 which is incorporated herein in full by specific reference.

In a variation, the present invention provides unit doses which contain oxycodone and an oxycodone antagonist effective to prevent tampering. In this respect, reference is made to WO 0313433 which is incorporated herein in full by specific reference. In particular, the unit dose can contain oxycodone and naltrexone. Other opioid antagonists which are known in the art can be used, for example naloxone.

To this end, another aspect of the present invention provides extruded multiparticulates of oxycodone, and extruded multiparticulates of oxycodone antagonist such as naltrexone or naloxone. The naltrexone multiparticulates do not release naltrexone on conventional administration, and for example have a non-release coating. Both populations are preferably visually and physically identical.

An important aspect of this invention is a capsule with a unit dose fill of less than 500 mg, comprising up to about 350 mg of oxycodone multiparticulates, and up to about 200 mg of tamper-proof oxycodone antagonist. For example, there can be 120 to 300 mg of oxycodone multiparticulates, and 125 to 175 mg of tamper-proof oxycodone antagonist multiparticulates.

BRIEF DESCRIPTION OF THE DRAWINGS

Reference is made to the accompanying drawings, wherein.

EXAMPLES OF THE INVENTION

Standardised Conditions

For the following experimental work, standardised conditions were established for the extrusion of oxycodone hydrochloride blends. Unless specified otherwise, the extruder was a Leistritz Micro 18 running at a screw speed of 140 rpm, with a feed rate of 2.6 kg/h producing pellets of 1 mm diameter and 1 mm length.

Figure 1:
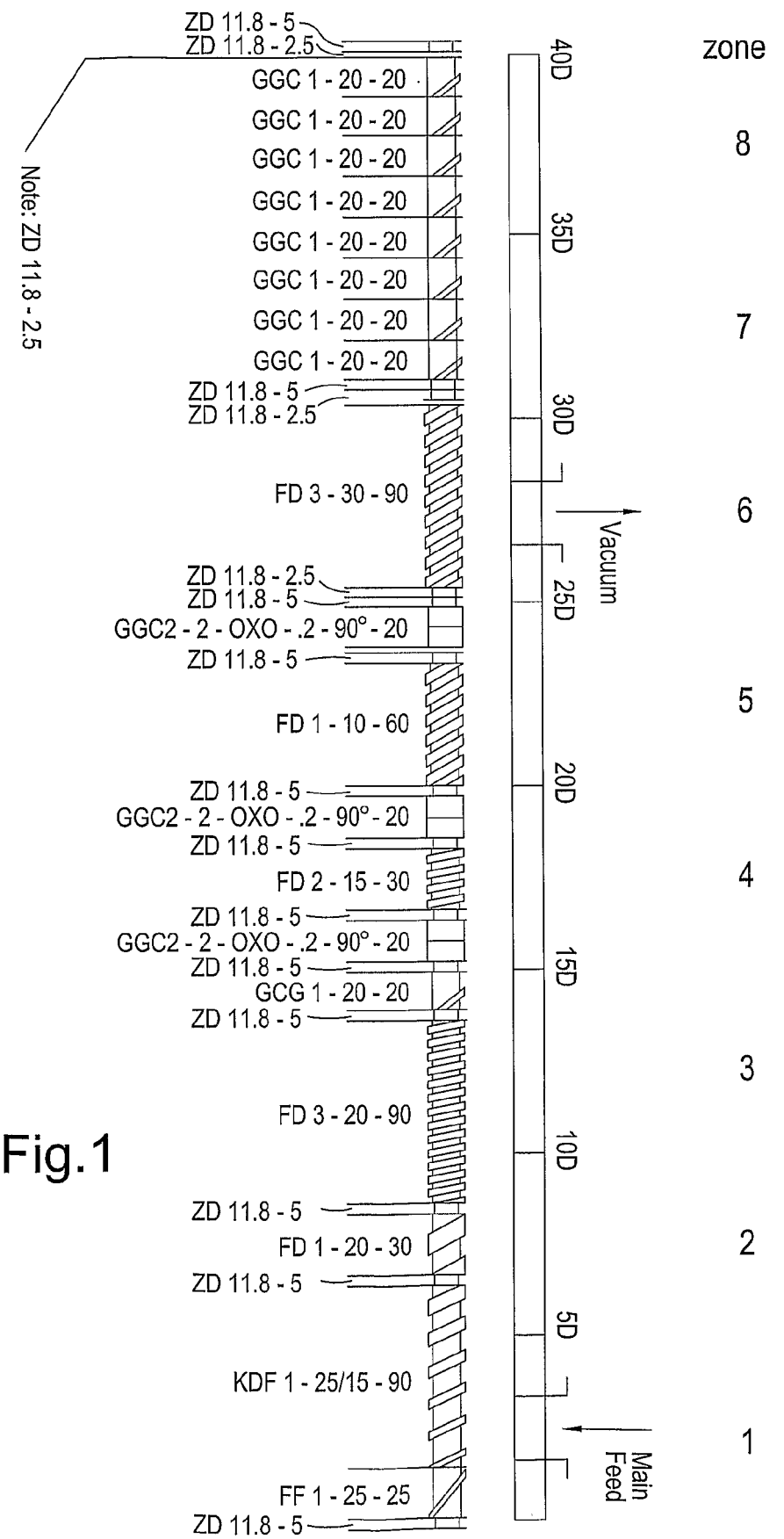
FIG. 1 is a schematic representation of one of the screw trains of the Leistritz Micro 18 twin screw extruder used in the Examples.
Figure 2:
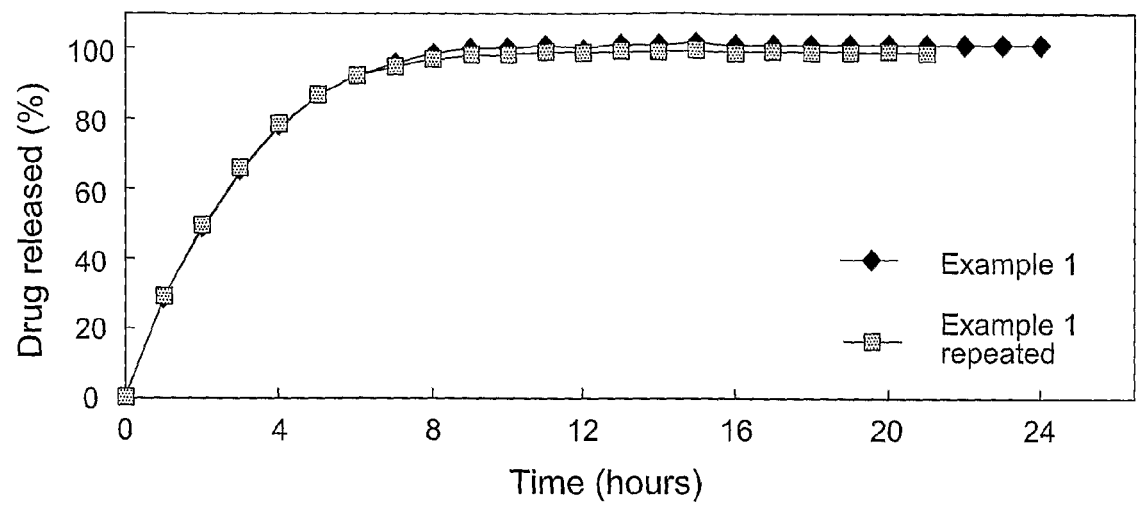
FIG. 2 provides in vitro dissolution data for the oxycodone extruded multiparticulates of Example 1 tested in simulated gastric fluid at pH 1.2.
Figure 3:
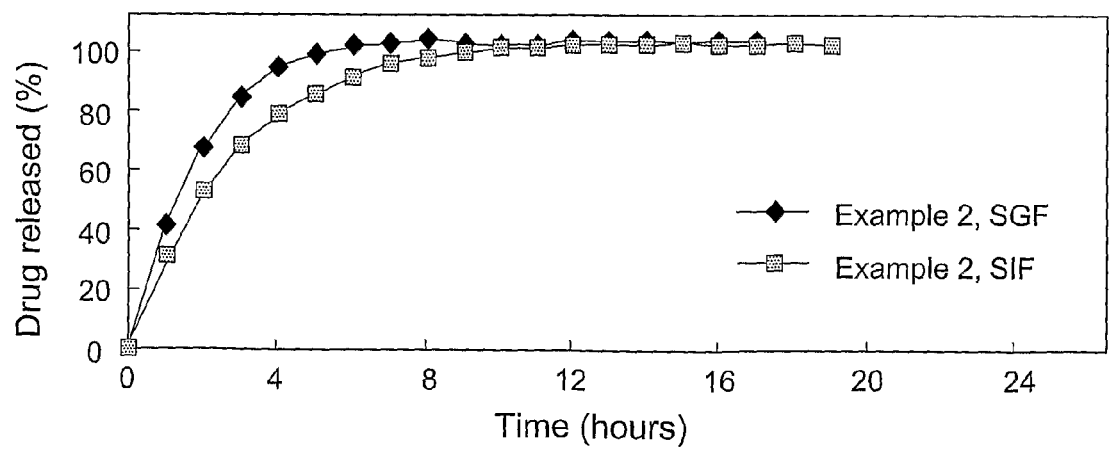
FIG. 3 provides in vitro dissolution data for the oxycodone extruded multiparticulates of Example 2 tested in both simulated gastric fluid at pH 1.2 and simulated intestinal fluid at pH 6.8.
Figure 4:
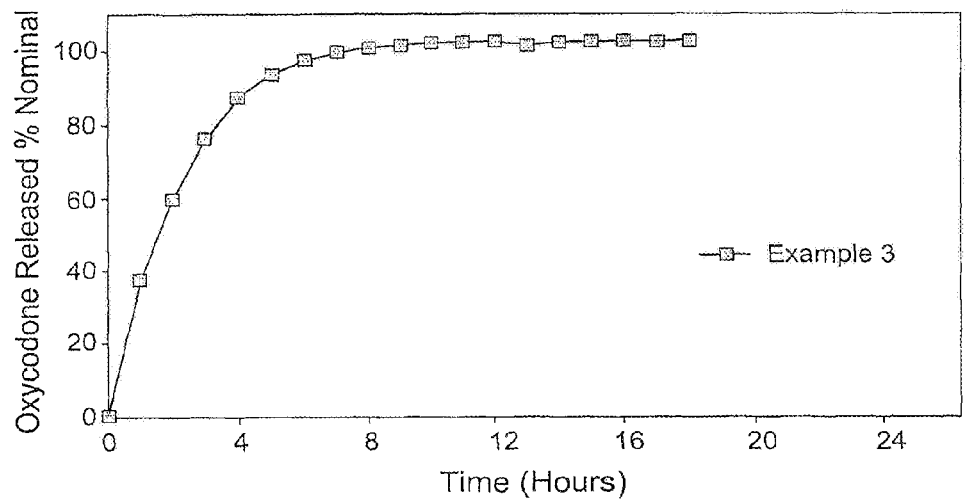
FIG. 4 provides in vitro dissolution data for the oxycodone extruded multiparticulates of Example 3 tested in simulated gastric fluid at pH 1.2.

The design of the screw is shown in FIG. 1 using components indicated by the manufacturing codes of the distributor Leistritz USA. The aim is to optimise the mixture by adding extra mixing elements 'GGC2' or 'ZS' to avoid mixing problems, and to increase the residence time by including 'FD' elements to avoid wetting problems.

The extruder comprises ten zones, with zone 1 extending from 0 to 5 D on FIG. 1; zone 2 extending from 5 D to 10 D on FIG. 1, and so on up to zone 8 extending from 35 D to 40 D, and then zones 9 and 10 are at the extruder head.

Typical batch zone temperatures are given later.
Release Rate Studies

The oxycodone extruded multiparticulates of Examples 1 to 7 were tested for dissolution using Ph.Eur. basket dissolution apparatus at 37° C., 100 rpm in 900 ml of USP simulated gastric fluid, SGF, at pH 1.2 without enzyme. Standard HPLC procedures were used for assay.

Additionally, the oxycodone extruded multiparticulates of Example 2 were tested for dissolution using Ph.Eur. basket dissolution apparatus at 37° C., 100 rpm in 900 ml of simulated intestinal fluid, SIF, at pH 6.8 without enzyme. Again, standard HPLC procedures were used for assay.

The in vitro release rates were measured, and gave the results plotted in the accompanying FIGS. 2 to 5.

Examples 1 to 3

The following trial batches with a drug load of 8.3% w/w were prepared, where the weights are mg per unit dose.

| | Quantity (mg) per unit dose weight (% of total) | | |
|---|---|---|---|
| | Example 1 | Example 2 | Example 3 |
| Oxycodone HCl | 10.0 (8.3%) | 10.0 (8.3%) | 10.0 (8.3%) |
| Eudragit RS PO | 79.0 (65.8%) | 71.0 (59.2%) | 74.0 (61.7%) |
| Eudragit RL PO | 18.0 (15.0%) | 26.0 (21.7%) | 18.0 (15.0%) |
| Stearyl alcohol | 13.0 (10.8%) | 13.0 (10.8%) | 18.0 (15.0%) |
| Total | 120 mg | 120 mg | 120 mg |

Typical batch zone temperatures (° C.), melt pressures and torque used in processing the formulations of Examples 1 to 3 were as follows:

| | Zone temperature (° C.) | | | | | | Melt Pressure | |
|---|---|---|---|---|---|---|---|---|
| Example | 1 | 2 | 3-6 | 7-8 | 9 | 10 | (bar) | Torque (%) |
| 1 | 14 | 40 | 125 | 115 | 120 | 125 | 74-85, e.g. 74-81, 75-83 or 79-85 | 82-91, e.g. 82-85, 83-87 or 86-91 |
| 2 | 14 | 40 | 125 | 115 | 120 | 125 | 72-90 e.g. 72-79 or 83-90 | 85-92 e.g. 88-92 |
| 3 | 14 | 40 | 103 | 102 | 105 | 105 | 83-90 | 87-90 |

The formulation of Example 3 is the currently preferred 8.3% w/w drug load product.

Examples 4 and 5

Q12Hr formulations were prepared with a drug load of 30.3% w/w, to enable filling into size 1 capsules: 40 mg in 132 mg dose weight and 80 mg in 264 mg dose weight. The component levels enabled relatively low processing temperatures to be achieved. The conveyor and pelletiser speeds were optimised during processing. The processing conditions for Examples 4 and 5 are shown.

Example 4 is a preferred 30.3% w/w drug load product.

| | Quantity (mg) per unit dose weight (% of total) | |
|---|---|---|
| | Example 4 | Example 5 |
| Oxycodone HCl | 40.0 (30.3%) | 40.0 (30.3%) |
| Eudragit RS PO | 68.0 (51.5%) | 66.0 (50.0%) |
| Eudragit RL PO | 8.0 (6.1%) | 7.0 (5.3%) |
| Stearyl alcohol | 16.0 (12.1%) | 19.0 (14.4%) |
| Total | 132 mg | 132 mg |

Example 4

Extruder Processing Conditions

| | |
|---|---|
| Extruder: | Leistritz Micro 18 |
| Screw configuration: | See diagram in FIG. 1 |
| Feed rate (kg/hour): | 2.0 |
| Screw speed (rpm): | 120 |
| Die plate orifice diameter (mm): | 1.0 (8 orifice plate) |
| Pellet dimensions: | 1.0 mm × 1.0 mm (range 0.8-1.2 mm) |

Example 4

| | Heating zone: | | | |
|---|---|---|---|---|
| | 1 | 2 | 3-8 | 9-10 |
| Temp* (° C.) | 14 | 40 | 107 | 109 |

Torque (%): 94-97
Melt Pressure (bar): 94-101
Die plate orifice depth (mm): 3.7

Example 5

Extruder Processing Conditions

| | |
|---|---|
| Extruder: | Leistritz Micro 18 |
| Screw configuration: | See diagram in FIG. 1 |
| Feed rate (kg/hour): | 2.6 |
| Screw speed (rpm): | 140 |
| Die plate orifice diameter (mm): | 1.0 (8 orifice plate) |
| Pellet dimensions: | 1.0 mm × 1.0 mm (range 0.8-1.2 mm) |

Example 5

| | Heating zone: | | | | |
|---|---|---|---|---|---|
| | 1 | 2 | 3-6 | 7-8 | 9-10 |
| Temp* (° C.) | 14 | 40 | 102-103 | 103 | 104 |

Torque (%): 81-84
Melt Pressure (bar): 79-83
Die plate orifice depth (mm): 3.7

Example 6

A formulation was prepared based on the batch of Example 5 with an adjusted level of plasticiser. Processing of this batch was carried out using an extrusion die plate with an orifice depth of 2.4 mm. Further improvements in processing conditions, i.e. melt pressure and screw torque, were obtained after adjustment of the extrusion die plate depth from 3.7 mm to 2.4 mm. The temperature and die plate conditions used are shown below.

| Batch number | Quantity (mg) per unit dose weight (% of total) Example 6 |
|---|---|
| Oxycodone HCl | 40.0 (30.3%) |
| Eudragit RSPO | 70.0 (53.0%) |
| Eudragit RLPO | 4.0 (3.0%) |
| Stearyl alcohol | 18.0 (13.6%) |
| Total | 132 mg |

Example 6

| | Heating zone: | | | | |
|---|---|---|---|---|---|
| | 1 | 2 | 3-6 | 7-8 | 9-10 |
| Temp* (° C.) | 14 | 40 | 102-103 | 102-103 | 104 |

Torque (%): 74-76
Melt Pressure (bar): 70-73
Die plate orifice depth (mm): 2.4

Figure 5:
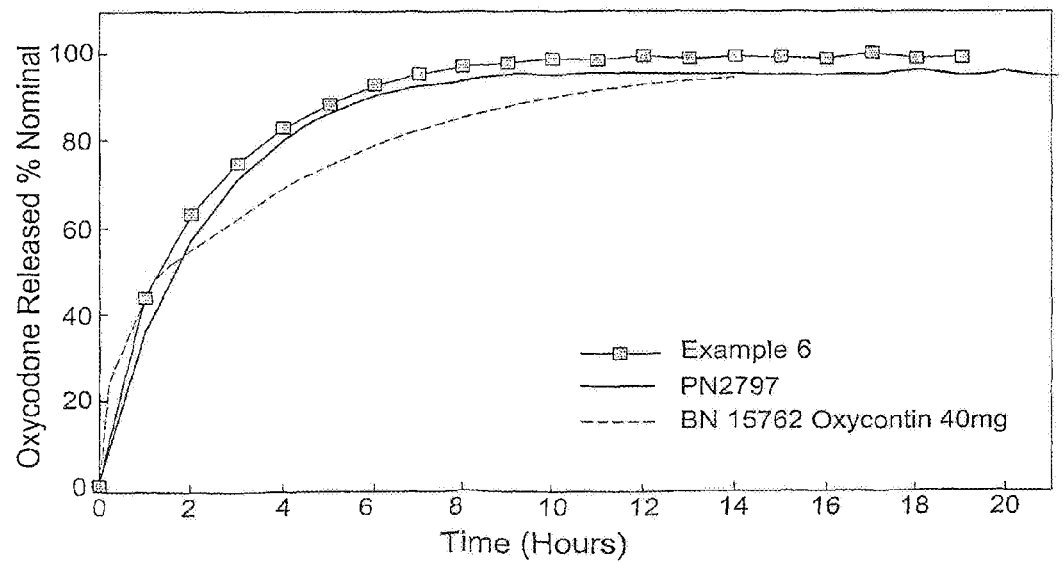
FIG. 5 provides in vitro dissolution data for the capsules of Example 6 compared with the target in vitro dissolution profile designated PN2797 (encapsulated product) and the in vitro dissolution profile for a commercial batch of OxyContin® 40 mg tablets.

Dissolution tests were carried out for the capsules of Example 6, also referred to as F764/61. As shown in FIG. 5, oxycodone dissolution profiles from this formulation compared well with the target profile designated PN2797 (encapsulated product). The profile for a commercial batch of OxyContin® 40 mg tablets is also given in FIG. 5.

Example 7

A further formulation, with a reduced content of stearyl alcohol, was designed to ensure improved stability to storage and minimise changes in the dissolution profiles during storage. This approach had previously been shown to improve the stability of the dissolution rate under accelerated storage conditions for 10/20 mg dose product formulations, e.g. 10 mg oxycodone hydrochloride in 120 mg capsule fill weight and 20 mg oxycodone hydrochloride in 240 mg capsule fill weight.

Example 7 is a preferred 30.3% w/w drug load product. Acceptable extrusion processing conditions could not be established on the Leistritz Micro 18 extruder due to the maximum torque limit being reached with this formulation. This formulation would, however, be recommended for processing on a Leistritz Micro 27 extruder, which is able to handle higher torque levels, to generate products with improved storage stability.

| Batch number | Quantity (mg) per unit dose weight (% of total) Example 7 |
|---|---|
| Oxycodone HCl | 40.0 (30.3%) |
| Eudragit RSPO | 71.0 (53.8%) |
| Eudragit RLPO | 5.0 (3.8%) |
| Stearyl alcohol | 16.0 (12.1%) |
| Total | 132 mg |

Example 8

Co-encapsulation of extruded oxycodone multiparticulates and extruded naltrexone multiparticulates can be used for a tamper resistant combination product.

Oxycodone multiparticulates and naltrexone multiparticulates as described in WO 03013433 may be filled into capsules using a single or dual stage filling process. The quantity of naltrexone multiparticulates which may be filled is 150 mg, containing 8 mg of naltrexone. The recommended fill weights of oxycodone multiparticulates to achieve oxycodone doses ranging from 10 mg to 40 mg are as follows (see also the following table):

1. 120 mg and 240 mg of 8.3% (w/w) drug loaded multiparticulates for oxycodone doses of 10 mg and 20 mg, respectively.
2. 160 mg of 25% (w/w) drug loaded multiparticulates for an oxycodone dose of 40 mg.
3. 132 mg of 30.3% (w/w) drug loaded multiparticulates for an oxycodone dose of 40 mg.

In addition, 5 mg and 80 mg oxycodone doses may also be considered, with respective capsule fill weights as follows:

1. 60 mg of 8.3% (w/w) drug loaded multiparticulates for an oxycodone dose of 5 mg,
2. 320 mg of 25% (w/w) drug loaded multiparticulates for an oxycodone dose of 80 mg.
3. 264 mg of 30.3% (w/w) drug loaded multiparticulates for an oxycodone dose of 80 mg.

Capsule filling of the required proportions of oxycodone and naltrexone multiparticulates may be achieved using either a single stage process or preferably a dual stage filling process. In the single stage filling process, the respective proportions of multiparticulates may be pre-blended and filled into capsules either by manual or preferably automated processes. By the preferred dual stage filling process, one type of multiparticulates can be filled in a first stage, either by manual or preferably automated processes. The second type of multiparticulates can then be filled in the second filling stage, again either by manual or preferably automated processes.

The theoretical fill weights for a range of capsule strengths based on drug loading are given in the following table.

| oxycodone mg per capsule | Oxycodone loading 8.3% w/w | |
|---|---|---|
| | oxycodone multi-particulates (mg) | oxycodone and naltrexoneØ multi-particulates (mg) |
| 10 | 120 | 270 (capsule Size 1) |
| 20 | 240 | 390 (capsule Size 0) |
| 40 | 480 | 630 (can not be filled) |
| 5+ | 60* | 210 (capsule Size 1) |
| 80+ | 960 | 1110 (can not be filled) |

*Weight below assumed minimum possible capsule fill weight.
+Included as an illustration of possibilities, if lower or higher strengths in the range are required.
Ø120 mg naltrexone multiparticulates + 20% coat.

| oxycodone mg per capsule | Oxycodone loading 25% w/w | |
|---|---|---|
| | oxycodone multi-particulates (mg) | oxycodone and naltrexoneØ multi-particulates (mg) |
| 10 | 40* | Low to fill |
| 20 | 80 | 230 (capsule Size 1) |
| 40 | 160 | 310 (capsule Size 0) |
| 5+ | 20* | Low to fill |
| 80+ | 320 | 470 (capsule Size 0E) |

*Weight below assumed minimum possible capsule fill weight.
+Included as an illustration of possibilities, if lower or higher strengths in the range are required.
Ø120 mg naltrexone multiparticulates + 20% coat.

The invention claimed is:

1. A unit dose form comprising melt extruded, controlled release multiparticulates, said multiparticulates comprising: (a) a pharmaceutically active agent; (b) an insoluble ammonium methacrylate copolymer; (c) a water permeability modifier; and (d) a non-dominating plasticiser, wherein the amount of non-dominating plasticiser is 1 to 15% based on the total weight of ingredients (a)-(d), and wherein said multiparticulates do not include a dominating or non-dominating lubricant selected from stearic acid, glyceryl behenate, magnesium stearate, calcium stearate, talc or fused silica, in an amount sufficient to provide substantial lubrication during processing.

2. The unit dose form according to claim 1, wherein the pharmaceutically active agent is 5 to 400 mg of oxycodone hydrochloride.

3. The unit dose form according to claim 1, suited for administration once daily.

4. The unit dose form according to claim 1, suited for administration twice daily.

5. The unit dose form according to claim 1 comprising a capsule with a fill of the multiparticulates.

6. The unit dose form according to claim 1, wherein the pharmaceutically active agent is oxycodone.

7. A method of providing analgesia to a patient which comprises administering an effective amount of the unit dose form according to claim 1 wherein the pharmaceutically active agent is an analgesic.

8. The unit dose form according to claim 2, suited for administration once daily.

9. The unit dose form according to claim 2, suited for administration twice daily.

10. The unit dose form according to claim 2 comprising a capsule with a fill of the multiparticulates.

11. The unit dose form according to claim 2, further comprising an oxycodone antagonist.

12. A method of providing analgesia to a patient which comprises administering an effective amount of the unit dose form according to claim 2.

13. Melt extruded, controlled release multiparticulates, said multiparticulates comprising: (a) a pharmaceutically active agent; (b) an insoluble ammonium methacrylate copolymer; (c) a water permeability modifier; and (d) a non-dominating plasticiser, wherein the amount of non-dominating plasticiser is 1 to 15% based on the total weight of ingredients (a)-(d), and wherein said multiparticulates do not include a dominating or non-dominating lubricant selected from stearic acid, glyceryl behenate, magnesium stearate, calcium stearate, talc or fused silica, in an amount sufficient to provide substantial lubrication during processing by melt extrusion.

14. Multiparticulates consisting essentially of (a) a pharmaceutically active agent, (b) an insoluble ammonium methacrylate copolymer, (c) a water permeability modifier, and (d) a non-dominating plasticiser, wherein the amount of the non-dominating plasticiser is 1 to 15% based on the total weight of ingredients (a)-(d).

15. Multiparticulates according to claim 13, wherein the pharmaceutically active agent is an opioid.

16. Multiparticulates according to claim 15, wherein the pharmaceutically active agent is oxycodone free base or a pharmaceutically acceptable salt thereof.

17. Multiparticulates according to claim 13, wherein the ammonium methacrylate copolymer is a copolymer of acrylic and methacrylic esters, with a low content of quaternary ammonium groups, and having an average molecular weight of 150,000.

18. Multiparticulates according to claim 13, wherein the non-dominating plasticiser is cetyl alcohol, stearyl alcohol, cetostearyl alcohol, sorbitol, sucrose, high molecular weight polyethylene glycol, dibutyl sebacate, tributyl citrate, triethyl citrate, propylene glycol or low molecular weight polyethylene glycol.

19. Multiparticulates according to claim 13, wherein the water permeability modifier is an insoluble hydrophilic wicking agent, a gelling agent which hydrates to form a gel, a high molecular weight polyethylene glycol, or a water permeable ammonium methacrylate copolymer.

20. Multiparticulates according to any one of claims 13-19 comprising on a w/w basis: 8 to 30% pharmaceutically active agent, 55 to 70% insoluble ammonium methacrylate copolymer, 1 to 15% non-dominating plasticiser, and 10 to 20% water permeability modifier.

21. Multiparticulates according to claim 13, wherein the pharmaceutically active agent is alfentanil, allylprodine, alphaprodine, anileridine, benzylmorphine, bezitramide, buprenorphine, butorphanol, clonitazene, codeine, cyclazocine, desomorphine, dextromoramide, dezocine, diacetylmorphine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydroxypethidine, isomethadone, ketobemidone, levorphanol, levophenacylmorphan, lofentanil, meperidine, meptazinol, metazocine, methadone, metopon, morphine, morphine-6-glucuronide, myrophine, nalbuphine, narceine, nicomorphine, norlevorphanol, normethadone, normorphine, norpipanone, noroxymorphone, opium, oxycodone, oxymorphone, papaveretum, pentazocine, phenadoxone, phenomorphan, phenazocine, phenoperidine, piminodine, piritramide, propheptazine, promedol, properidine, propiram, propoxyphene, remifentanil, sufentanil, tilidine, tramadol, atorvastatin, 6-[4,4-bis(fluorophenyl)-3-(1-methyl-1H-tetrazol-5-yl)-1,3-butadienyl]-3,4,5,6-tetrahydro-4-hydroxy-2H-pyran-2-one, 3-(12-carboxy-12-methyltridecyl)-3-hydroxyglutaric acid, cerivastatin, dalvastatin, 3,5-dihydroxy-9,9-diphenyl-6,8-nonadienoic acid methyl ester, fluindostatin, fluvastatin, 6-(2-(4'-fluoro-3,3',5-trimethyl-2-biphenylyl)vinyl]4-hydroxy-2-oxotetrahydropyran, 6-[2-[4-(-fluorophenyl)-2-isopropyl-6-phenyl-3-pyridyl]vinyl]-3,4,5,6-tetrahydro-4-hydroxy-2H-pyran-2-one, lovastatin, mevastatin, mevinolinic acid, monacolin J, monacolin L, pitavastatin, pravastatin, rosuvastatin, simvastatin, aminoglycosides, carbapenems, cephalosporins, cephamycins, folic acid inhibitors, lincosamides, macrolides, monobactams, nitroimidazoles, penicillins, quinolones, streptogramin, sulphonamides, tetracyclines, or their pharmaceutically acceptable salts thereof.

22. Multiparticulates according to claim 21, wherein the oxycodone is present as a pharmaceutically acceptable salt.

23. Multiparticulates according to claim 22, wherein the oxycodone is present as oxycodone hydrochloride.

24. Multiparticulates according to claim 18, wherein the non-dominating plasticiser is stearyl alcohol.

25. Multiparticulates according to claim 19, wherein the water permeability modifier is a water permeable ammonium methacrylate copolymer.

26. The unit dose form according to claim 6, further comprising an oxycodone antagonist.

27. The unit dose form according to claim 1, wherein the pharmaceutically active agent is an opioid agonist.

28. Multiparticulates according to claim 13, wherein the pharmaceutically active agent is an opioid agonist.

* * * * *